United States Patent
Kim et al.

(10) Patent No.: US 11,498,965 B2
(45) Date of Patent: Nov. 15, 2022

(54) ANTI-CD3 ANTIBODY AND PHARMACEUTICAL COMPOSITION FOR CANCER TREATMENT COMPRISING SAME

(71) Applicants: GREEN CROSS CORPORATION, Yongin-si (KR); MOGAM INSTITUTE FOR BIOMEDICAL RESEARCH, Yongin-si (KR)

(72) Inventors: Ki Su Kim, Yongin-si (KR); Jun Hong Jeong, Yongin-si (KR); Ae Rin Yoon, Yongin-si (KR); Eun Jung Song, Yongin-si (KR); Hye Ji Choi, Yongin-si (KR); Ok Jae Lim, Yongin-si (KR); Yun Jung Lee, Yongin-si (KR); Hyung Kwon Lim, Yongin-si (KR); Jong Wha Won, Yongin-si (KR)

(73) Assignees: GREEN CROSS CORPORATION, Yongin-si (KR); MOGAM INSTITUTE FOR BIOMEDICAL RESEARCH, Yongin-si (KR)

( * ) Notice: Subject to any disclaimer, the term of this patent is extended or adjusted under 35 U.S.C. 154(b) by 212 days.

(21) Appl. No.: 16/754,431

(22) PCT Filed: Oct. 22, 2018

(86) PCT No.: PCT/KR2018/012492
§ 371 (c)(1),
(2) Date: Apr. 8, 2020

(87) PCT Pub. No.: WO2019/078697
PCT Pub. Date: Apr. 25, 2019

(65) Prior Publication Data
US 2020/0317779 A1    Oct. 8, 2020

(30) Foreign Application Priority Data
Oct. 20, 2017 (KR) .......... 10-2017-0136564

(51) Int. Cl.
*C07K 16/28* (2006.01)
*A61K 39/00* (2006.01)

(52) U.S. Cl.
CPC .......... *C07K 16/2809* (2013.01); *A61K 39/00* (2013.01); *C07K 2317/24* (2013.01); *C07K 2317/56* (2013.01)

(58) Field of Classification Search
None
See application file for complete search history.

(56) References Cited

U.S. PATENT DOCUMENTS

| 8,846,042 B2 * | 9/2014 | Zhou ............... A61P 43/00 |
| | | 530/387.3 |
| 2015/0166661 A1 | 6/2015 | Chen et al. |

FOREIGN PATENT DOCUMENTS

| EP | 3 177 646 | 6/2017 |
| JP | 2016-529882 A | 9/2016 |
| KR | 10-2005-0000376 A | 1/2005 |
| KR | 10-2014-0033107 A | 3/2014 |
| KR | 10-2015-0046789 A | 4/2015 |
| KR | 10-2017-0010863 A | 2/2017 |
| WO | 2007/042261 A2 | 4/2007 |
| WO | 2012/158818 A2 | 11/2012 |
| WO | 2015/001085 A1 | 1/2015 |
| WO | 2016/020444 A1 | 2/2016 |
| WO | 2017/136659 A2 | 8/2017 |
| WO | 2018/199593 A1 | 11/2018 |

OTHER PUBLICATIONS

Vajdos et al. (J Mol Biol. Jul. 5, 2002;320(2):415-28). (Year: 2002).*
Bedouelle et al. (FEBS J. Jan. 2006;273(1):34-46). (Year: 2006).*
Brown et al. (J Immunol. May 1, 1996;156(9):3285-91). (Year: 1996).*
Colman (Research in Immunology, 145:33-36, 1994). (Year: 1994).*
Rudikoff et al. (Proc. Natl. Acad. Sci. USA, 79: 1979-1983, Mar. 1982). (Year: 1982).*
International Search Report for PCT/KR2018/012492 dated May 20, 2019 [PCT/ISA/210].

* cited by examiner

*Primary Examiner* — Zachary S Skelding
(74) *Attorney, Agent, or Firm* — Sughrue Mion, PLLC

(57) ABSTRACT

The present invention relates to an anti-CD3 antibody and a pharmaceutical composition for cancer treatment comprising same. The antibody according to the present invention has high affinity and specificity for CD3 and thus can be effectively used in cancer prevention or treatment.

16 Claims, 2 Drawing Sheets
Specification includes a Sequence Listing.

[Fig. 1]
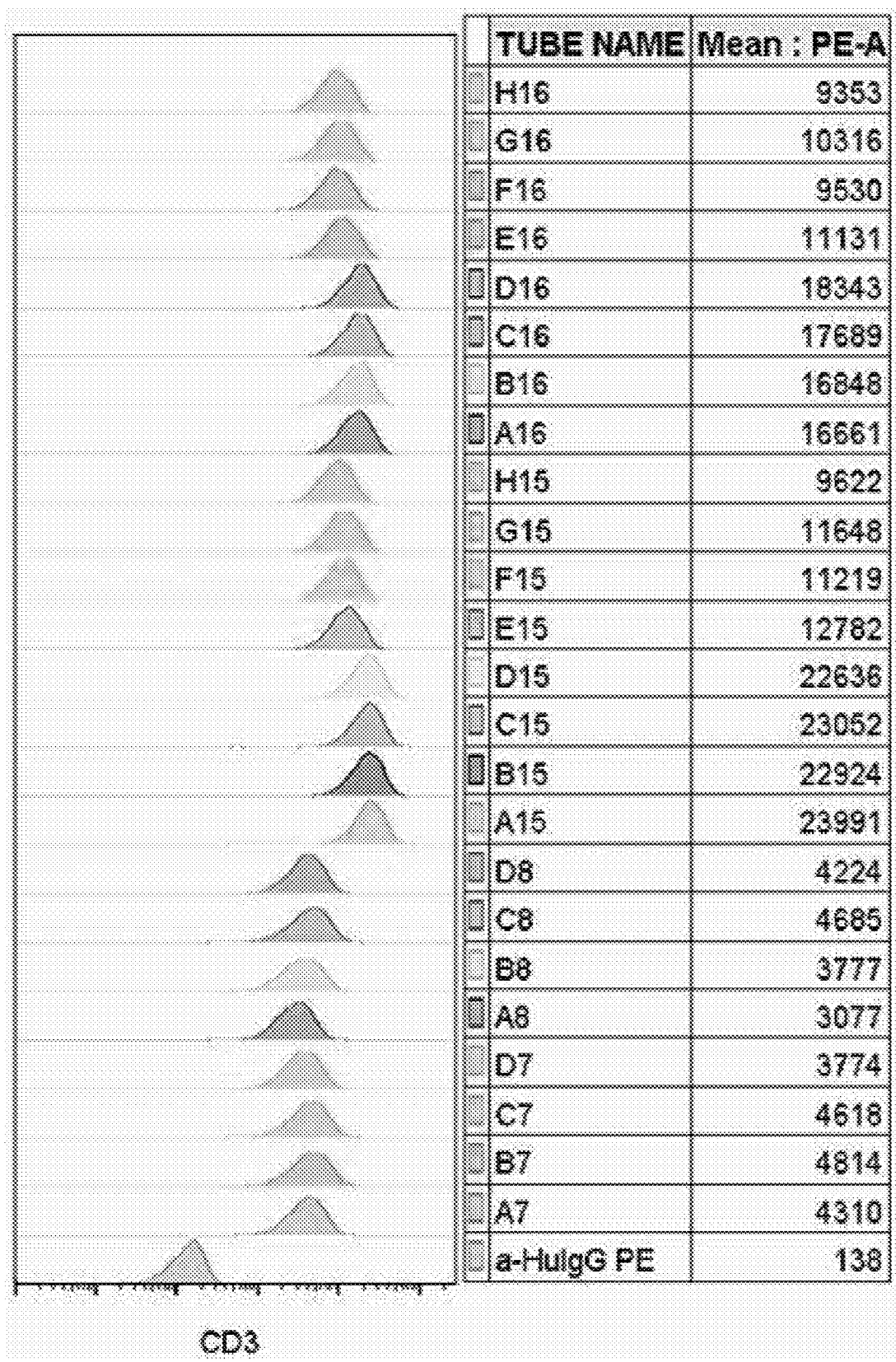

[Fig. 2]
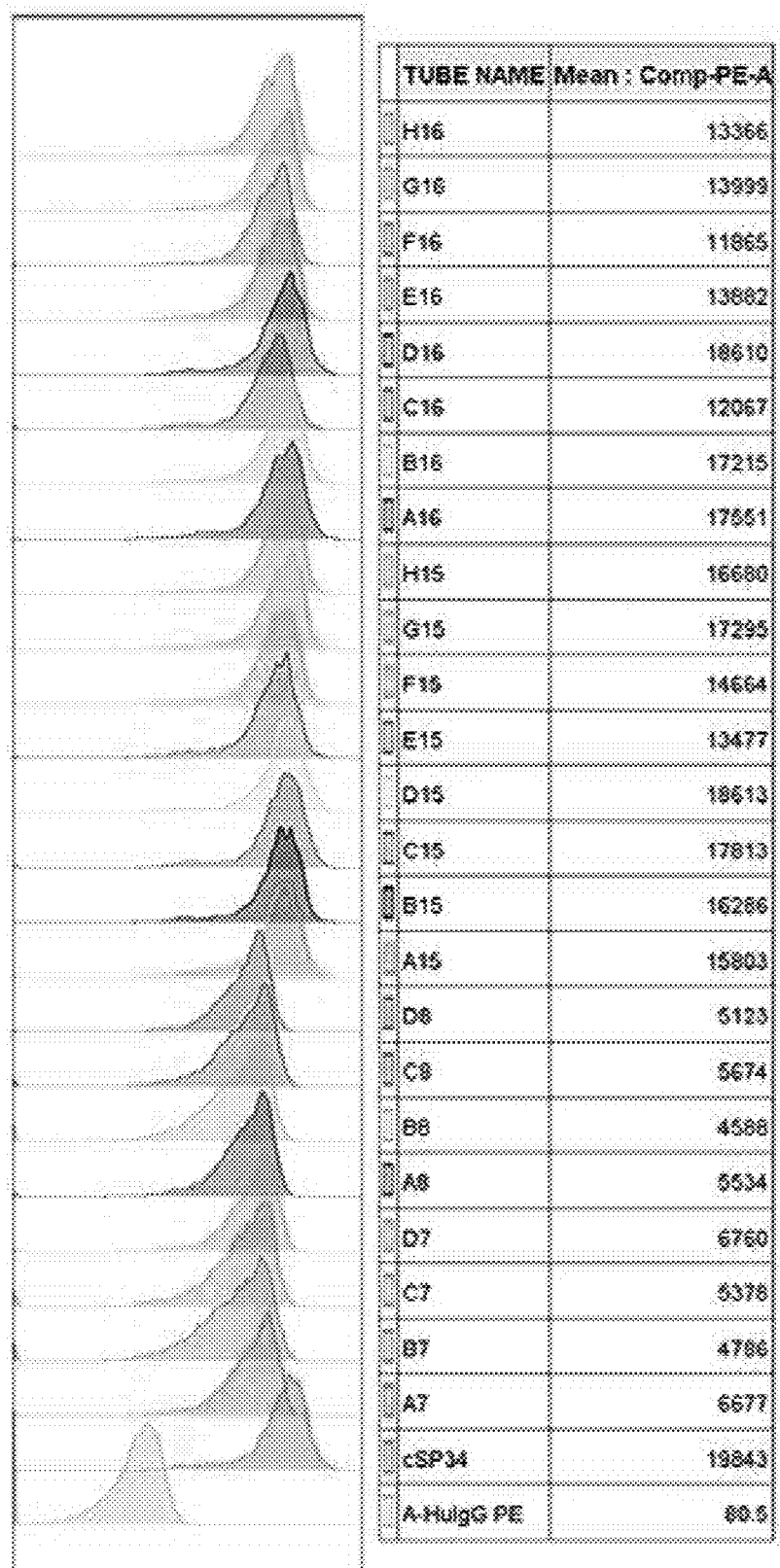

```
                        SEQUENCE LISTING

<160> NUMBER OF SEQ ID NOS: 34

<210> SEQ ID NO 1
<211> LENGTH: 110
<212> TYPE: PRT
<213> ORGANISM: Artificial Sequence
<220> FEATURE:
<223> OTHER INFORMATION: VL-1 clone of humanized SP34

<400> SEQUENCE: 1

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Thr
        35                  40                  45

Leu Ile Tyr Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 2
<211> LENGTH: 110
<212> TYPE: PRT
<213> ORGANISM: Artificial Sequence
<220> FEATURE:
<223> OTHER INFORMATION: VL-2 clone of humanized SP34

<400> SEQUENCE: 2

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Thr
        35                  40                  45

Leu Ile Tyr Gly Thr Asn Lys Arg Ala Pro Trp Thr Pro Ala Arg Phe
    50                  55                  60

Ser Gly Ser Leu Leu Gly Asp Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly
            100                 105                 110
```

<210> SEQ ID NO 3
<211> LENGTH: 110
<212> TYPE: PRT
<213> ORGANISM: Artificial Sequence
<220> FEATURE:
<223> OTHER INFORMATION: VL-3 clone of humanized SP34

<400> SEQUENCE: 3

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Thr
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 4
<211> LENGTH: 110
<212> TYPE: PRT
<213> ORGANISM: Artificial Sequence
<220> FEATURE:
<223> OTHER INFORMATION: VL-4 clone of humanized SP34

<400> SEQUENCE: 4

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Thr
        35                  40                  45

Leu Ile Gly Gly Thr Asn Lys Arg Ala Pro Trp Thr Pro Ala Arg Phe
    50                  55                  60

Ser Gly Ser Leu Leu Gly Asp Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 5
<211> LENGTH: 110
<212> TYPE: PRT
<213> ORGANISM: Artificial Sequence
<220> FEATURE:
<223> OTHER INFORMATION: VL-5 clone of humanized SP34

<400> SEQUENCE: 5

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Gly
                35                  40                  45

Leu Ile Tyr Gly Thr Asn Lys Arg Ala Pro Trp Thr Pro Ala Arg Phe
            50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly
                100                 105                 110

<210> SEQ ID NO 6
<211> LENGTH: 110
<212> TYPE: PRT
<213> ORGANISM: Artificial Sequence
<220> FEATURE:
<223> OTHER INFORMATION: VL-6 clone of humanized SP34

<400> SEQUENCE: 6

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Phe Gln Gln Lys Pro Gly Gln Ala Pro Arg Gly
                35                  40                  45

Leu Ile Tyr Gly Thr Asn Lys Arg Ala Pro Trp Thr Pro Ala Arg Phe
            50                  55                  60

Ser Gly Ser Leu Leu Gly Asp Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly
                100                 105                 110

<210> SEQ ID NO 7
<211> LENGTH: 110
<212> TYPE: PRT
<213> ORGANISM: Artificial Sequence
<220> FEATURE:
<223> OTHER INFORMATION: VL-7 clone of humanized SP34

<400> SEQUENCE: 7

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Phe Gln Gln Lys Pro Gly Gln Ala Pro Arg Gly
                35                  40                  45

Leu Ile Gly Gly Thr Asn Lys Arg Ala Pro Trp Thr Pro Ala Arg Phe
            50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly
                100                 105                 110

<210> SEQ ID NO 8

```
<211> LENGTH: 110
<212> TYPE: PRT
<213> ORGANISM: Artificial Sequence
<220> FEATURE:
<223> OTHER INFORMATION: VL-8 clone of humanized SP34

<400> SEQUENCE: 8

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Asp Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 9
<211> LENGTH: 110
<212> TYPE: PRT
<213> ORGANISM: Artificial Sequence
<220> FEATURE:
<223> OTHER INFORMATION: VL-9 clone of humanized SP34

<400> SEQUENCE: 9

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Thr
        35                  40                  45

Leu Ile Tyr Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 10
<211> LENGTH: 110
<212> TYPE: PRT
<213> ORGANISM: Artificial Sequence
<220> FEATURE:
<223> OTHER INFORMATION: VL-10 clone of humanized SP34

<400> SEQUENCE: 10

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Thr
        35                  40                  45
```

```
Leu Ile Tyr Gly Thr Asn Lys Arg Ala Pro Trp Thr Pro Ala Arg Phe
 50                  55                  60

Ser Gly Ser Leu Leu Gly Asp Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly
            100                 105                 110

<210> SEQ ID NO 11
<211> LENGTH: 110
<212> TYPE: PRT
<213> ORGANISM: Artificial Sequence
<220> FEATURE:
<223> OTHER INFORMATION: VL-11 clone of humanized SP34

<400> SEQUENCE: 11

Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
                 20                  25                  30

Asn Tyr Ala Asn Trp Val Gln Gln Lys Pro Gly Gln Ala Pro Arg Thr
             35                  40                  45

Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly
            100                 105                 110

<210> SEQ ID NO 12
<211> LENGTH: 110
<212> TYPE: PRT
<213> ORGANISM: Artificial Sequence
<220> FEATURE:
<223> OTHER INFORMATION: VL-12 clone of humanized SP34

<400> SEQUENCE: 12

Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
                 20                  25                  30

Asn Tyr Ala Asn Trp Val Gln Gln Lys Pro Gly Gln Ala Pro Arg Thr
             35                  40                  45

Leu Ile Gly Gly Thr Asn Lys Arg Ala Pro Trp Thr Pro Ala Arg Phe
 50                  55                  60

Ser Gly Ser Leu Leu Gly Asp Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly
            100                 105                 110

<210> SEQ ID NO 13
<211> LENGTH: 110
<212> TYPE: PRT
<213> ORGANISM: Artificial Sequence
```

<220> FEATURE:
<223> OTHER INFORMATION: VL-13 clone of humanized SP34

<400> SEQUENCE: 13

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Tyr Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 14
<211> LENGTH: 110
<212> TYPE: PRT
<213> ORGANISM: Artificial Sequence
<220> FEATURE:
<223> OTHER INFORMATION: VL-14 clone of humanized SP34

<400> SEQUENCE: 14

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Tyr Gly Thr Asn Lys Arg Ala Pro Trp Thr Pro Ala Arg Phe
    50                  55                  60

Ser Gly Ser Leu Leu Gly Asp Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 15
<211> LENGTH: 110
<212> TYPE: PRT
<213> ORGANISM: Artificial Sequence
<220> FEATURE:
<223> OTHER INFORMATION: VL-15 clone of humanized SP34

<400> SEQUENCE: 15

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

```
Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly
            100                 105                 110

<210> SEQ ID NO 16
<211> LENGTH: 110
<212> TYPE: PRT
<213> ORGANISM: Artificial Sequence
<220> FEATURE:
<223> OTHER INFORMATION: VL-16 clone of humanized SP34

<400> SEQUENCE: 16

Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
             35                  40                  45

Leu Ile Gly Gly Thr Asn Lys Arg Ala Pro Trp Thr Pro Ala Arg Phe
 50                  55                  60

Ser Gly Ser Leu Leu Gly Asp Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly
            100                 105                 110

<210> SEQ ID NO 17
<211> LENGTH: 110
<212> TYPE: PRT
<213> ORGANISM: Artificial Sequence
<220> FEATURE:
<223> OTHER INFORMATION: VL domain of mouse SP34

<400> SEQUENCE: 17

Gln Ala Val Val Thr Gln Glu Ser Ala Leu Thr Thr Ser Pro Gly Glu
 1               5                  10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
             35                  40                  45

Leu Ile Gly Gly Thr Asn Lys Arg Ala Pro Gly Val Pro Ala Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

Leu Trp Val Phe Gly Gly Gly Thr Lys Leu Thr Val Leu Gly
            100                 105                 110

<210> SEQ ID NO 18
<211> LENGTH: 125
<212> TYPE: PRT
<213> ORGANISM: Artificial Sequence
<220> FEATURE:
<223> OTHER INFORMATION: VH-A clone of humanized SP34
```

<400> SEQUENCE: 18

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125
```

<210> SEQ ID NO 19
<211> LENGTH: 125
<212> TYPE: PRT
<213> ORGANISM: Artificial Sequence
<220> FEATURE:
<223> OTHER INFORMATION: VH-B clone of humanized SP34

<400> SEQUENCE: 19

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125
```

<210> SEQ ID NO 20
<211> LENGTH: 125
<212> TYPE: PRT
<213> ORGANISM: Artificial Sequence
<220> FEATURE:
<223> OTHER INFORMATION: VH-C clone of humanized SP34

<400> SEQUENCE: 20

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45
```

```
Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Thr
65                  70                  75                  80

Ala Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 21
<211> LENGTH: 125
<212> TYPE: PRT
<213> ORGANISM: Artificial Sequence
<220> FEATURE:
<223> OTHER INFORMATION: VH-D clone of humanized SP34

<400> SEQUENCE: 21

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Ser Gly Lys Gly Leu Glu Trp Val
            35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Ser Gln Ser Thr
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 22
<211> LENGTH: 125
<212> TYPE: PRT
<213> ORGANISM: Artificial Sequence
<220> FEATURE:
<223> OTHER INFORMATION: VH-E clone of humanized SP34

<400> SEQUENCE: 22

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Ser Gly Lys Gly Leu Glu Trp Val
            35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110
```

```
Ala Tyr Trp Gly Gln Gly Thr Leu Val Thr Val Ser Ser
        115                 120                 125

<210> SEQ ID NO 23
<211> LENGTH: 125
<212> TYPE: PRT
<213> ORGANISM: Artificial Sequence
<220> FEATURE:
<223> OTHER INFORMATION: VH-F clone of humanized SP34

<400> SEQUENCE: 23

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 24
<211> LENGTH: 125
<212> TYPE: PRT
<213> ORGANISM: Artificial Sequence
<220> FEATURE:
<223> OTHER INFORMATION: VH-G clone of humanized SP34

<400> SEQUENCE: 24

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Thr
65                  70                  75                  80

Ala Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 25
<211> LENGTH: 125
<212> TYPE: PRT
<213> ORGANISM: Artificial Sequence
<220> FEATURE:
<223> OTHER INFORMATION: VH-H clone of humanized SP34
```

<400> SEQUENCE: 25

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Thr
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 26
<211> LENGTH: 125
<212> TYPE: PRT
<213> ORGANISM: Artificial Sequence
<220> FEATURE:
<223> OTHER INFORMATION: VH domain of mouse SP34

<400> SEQUENCE: 26

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 27
<211> LENGTH: 104
<212> TYPE: PRT
<213> ORGANISM: Artificial Sequence
<220> FEATURE:
<223> OTHER INFORMATION: lambda CL domain

<400> SEQUENCE: 27

Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Gly Ser Pro Val
        35                  40                  45

Lys Ala Gly Val Glu Thr Thr Lys Pro Ser Lys Gln Ser Asn Asn Lys
            50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys
            100

<210> SEQ ID NO 28
<211> LENGTH: 330
<212> TYPE: PRT
<213> ORGANISM: Artificial Sequence
<220> FEATURE:
<223> OTHER INFORMATION: IgG1 CH domain

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 29
<211> LENGTH: 14
<212> TYPE: PRT
<213> ORGANISM: Artificial Sequence
<220> FEATURE:
<223> OTHER INFORMATION: Amino acid seqeunce for anti-CD3 antibody of
      CDR1 (VL)

<400> SEQUENCE: 29

Arg Ser Ser Thr Gly Ala Val Thr Thr Ser Asn Tyr Ala Asn
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Amino acid seqeunce for anti-CD3 antibody of
      CDR2 (VL)

<400> SEQUENCE: 30

Gly Thr Asn Lys Arg Ala Pro
1               5

<210> SEQ ID NO 31
<211> LENGTH: 9
<212> TYPE: PRT
<213> ORGANISM: Artificial Sequence
<220> FEATURE:
<223> OTHER INFORMATION: Amino acid seqeunce for anti-CD3 antibody of
      CDR3 (VL)

<400> SEQUENCE: 31

Ala Leu Trp Tyr Ser Asn Leu Trp Val
1               5

<210> SEQ ID NO 32
<211> LENGTH: 10
<212> TYPE: PRT
<213> ORGANISM: Artificial Sequence
<220> FEATURE:
<223> OTHER INFORMATION: Amino acid seqeunce for anti-CD3 antibody of
      CDR1 (VH)

<400> SEQUENCE: 32

Gly Phe Thr Phe Asn Thr Tyr Ala Met Asn
1               5                   10

<210> SEQ ID NO 33
<211> LENGTH: 19
<212> TYPE: PRT
<213> ORGANISM: Artificial Sequence
<220> FEATURE:
<223> OTHER INFORMATION: Amino acid seqeunce for anti-CD3 antibody of
      CDR2 (VH)

<400> SEQUENCE: 33

Arg Ile Arg Ser Lys Tyr Asn Asn Tyr Ala Thr Tyr Tyr Ala Asp Ser
1               5                   10                  15

Val Lys Asp
```

```
<210> SEQ ID NO 34
<211> LENGTH: 16
<212> TYPE: PRT
<213> ORGANISM: Artificial Sequence
<220> FEATURE:
<223> OTHER INFORMATION: Amino acid seqeunce for anti-CD3 antibody of
      CDR3 (VH)

<400> SEQUENCE: 34

Val Arg His Gly Asn Phe Gly Asn Ser Tyr Val Ser Trp Phe Ala Tyr
1               5                   10                  15
```

ANTI-CD3 ANTIBODY AND PHARMACEUTICAL COMPOSITION FOR CANCER TREATMENT COMPRISING SAME

CROSS REFERENCE TO RELATED APPLICATIONS

This application is a National Stage of International Application No. PCT/KR2018/012492 filed Oct. 22, 2018, claiming priority based on Korean Patent Application No. 10-2017-0136564 filed Oct. 20, 2017.

TECHNICAL FIELD

The present invention relates to an anti-CD3 antibody and a pharmaceutical composition for treating cancer comprising same.

BACKGROUND ART

Among various causes of death, death from cancer occurs frequently, accounting for the second-largest proportion. Various attempts have been made to treat cancer in the past. Currently, regarding treatment methods for treating cancer, administration of an anticancer agent, irradiation, or surgical operation has been carried out. However, such treatment methods may be effective in the early stages of cancer, and have a poor therapeutic effect in a terminal cancer, when cancer has spread to other tissues, or when cancer has recurred.

In recent years, attention has been drawn to studies on adoptive cellular immunotherapy in which cancer is treated by subjecting lymphocytes taken from the peripheral blood of a patient to in vitro mass culture and then re-transplanting the cultured lymphocytes into the patient. Furthermore, a technique is also being developed in which toxic T cells specific for cancer cells are allowed to remove cancer cells by subjecting immune cells taken from the peripheral blood of a patient to in vitro mass proliferation, subjecting the proliferated immune cells to treatment with antigens such as cancer cell lysates so that the immune cells are activated, and then re-administering the resulting immune cells to the patient.

Technical Problem

The present invention is made to solve the above-mentioned problems of the prior art. An object of the present invention is to provide an antibody having high binding affinity to CD3 and a pharmaceutical composition having excellent cancer treatment efficacy using the same.

However, the problem to be solved by the present invention is not limited to the above-mentioned problems, and other problems which are not mentioned will be clearly understood by those skilled in the art from the following description.

Solution to Problem

In an aspect of the present invention, there is provided an antibody, comprising a light chain variable domain (VL domain) consisting of a sequence having at least 80% identity to an amino acid sequence of SEQ ID NO: 7, 8, 15, or 16 and a heavy chain variable domain (VH domain) consisting of a sequence having at least 80% identity to an amino acid sequence of any one of SEQ ID NOs: 18 to 25.

In another aspect of the present invention, there is provided a polynucleotide that encodes the light chain variable domain (VL domain) and the heavy chain variable domain (VH domain) of the antibody.

In yet another aspect of the present invention, there is provided an expression vector comprising the polynucleotide.

In still yet another aspect of the present invention, there is provided a host cell transformed with the expression vector.

In still yet another aspect of the present invention, there is provided a method for producing an antibody that specifically binds to CD3, comprising culturing the host cell.

In still yet another aspect of the present invention, there is provided a pharmaceutical composition for preventing or treating cancer, comprising the antibody or a fragment thereof.

Advantageous Effects of Invention

Owing to high affinity and specificity to CD3, an antibody of the present invention can be effectively used for prevention or treatment of cancer.

It is to be understood that the effect of the present invention is not limited to the above-described effects, and includes all effects that are deducible from the configuration of the invention described in the detailed description or the claims of the present invention.

BRIEF DESCRIPTION OF DRAWINGS

FIG. 1 illustrates results obtained by analyzing binding affinity to human T cells of antibodies according to an embodiment of the present invention.

FIG. 2 illustrates results obtained by analyzing binding affinity to monkey T cells of antibodies according to an embodiment of the present invention.

DETAILED DESCRIPTION OF INVENTION

Hereinafter, the present invention will be described in detail.

In an aspect of the present invention, there is provided an antibody comprising a light chain variable domain (VL domain) consisting of a sequence having at least 80% identity to an amino acid sequence of SEQ ID NO: 7, 8, 15, or 16 and a heavy chain variable domain (VH domain) consisting of a sequence having at least 80% identity to an amino acid sequence of any one of SEQ ID NOs: 18 to 25.

The light chain variable domain may consist of an amino acid sequence having at least 80%, preferably at least 90%, more preferably at least 95%, and most preferably at least 99% identity to an amino acid sequence of SEQ ID NO: 7, 8, 15, or 16.

In addition, the heavy chain variable domain may consist of an amino acid sequence having at least 80%, preferably at least 90%, more preferably at least 95%, and most preferably at least 99% identity to an amino acid sequence of any one of SEQ ID NOs: 18 to 25.

The antibody comprising the light chain variable domain and the heavy chain variable domain may specifically bind to cluster of differentiation 3 (CD3). Here, the antibody may have cross-reactivity to human and monkey CD3. That is, the CD3 may include, but is not limited to, human-derived CD3 and monkey-derived CD3.

As used herein, the term "CD3" may refer to a concept that collectively refers to CD3 itself, and any variant, isotype, and paralog thereof, which are present in an animal and preferably in a human and a monkey. In addition, as used herein, the term "human CD3" refers to human-derived CD3. As used herein, the term "monkey CD3" refers to monkey-derived CD3.

As used herein, the term "antibody" refers to an immunoglobulin (Ig) molecule that is immunologically reactive with a particular antigen, that is, a protein molecule that acts as a receptor that specifically recognizes an antigen. In addition, the antibody may be a whole antibody or an antibody fragment.

In the light and heavy chain variable domains, some amino acids may be substituted, inserted, and/or deleted as long as properties consistent with the object of the present invention, such as affinity and specificity to CD3, are maintained. For example, conservative substitutions of amino acids may occur in the light and/or heavy chain variable domains. The conservative substitution means a substitution of an original amino acid sequence with another amino acid residue having properties similar thereto.

For example, lysine, arginine, and histidine have similar properties in that they have a basic side chain, and aspartic acid and glutamic acid have similar properties in that they have an acidic side chain. In addition, glycine, asparagine, glutamine, serine, threonine, tyrosine, cysteine, and tryptophan have similar properties in that they have a non-charged polar side chain; alanine, valine, leucine, threonine, isoleucine, proline, phenylalanine, and methionine have similar properties in that they have a nonpolar side chain; and tyrosine, phenylalanine, tryptophan, and histidine have similar properties in that they have an aromatic side chain.

Therefore, it is apparent to those skilled in the art that the amino acid substitutions within the group of the amino acids having similar properties as described above will not cause any significant change in the properties. For this reason, antibodies that have undergone variation caused by a conservative substitution within the variable domain are also included in the scope of the present invention as long as such antibodies maintain properties of the antibody of the present invention.

On the other hand, the antibody may specifically bind to T cells, specifically to the surface of T cells, through specific binding with CD3. Here, the T cells may include, but are not limited to, human-derived T cells and monkey-derived T cells.

That is, when the antibody is present in the body, such an antibody may attract T cells through specific binding with CD3. Accordingly, the attracted T cells may induce immune responses in the vicinity thereof, and may further attack tumors such as cancer cells, and the like.

The light and heavy chain variable domains of the antibody may consist of complementarity determining regions (CDRs) and framework regions (FRs). Typically, CDRs provide binding specificity to specific antigens, and FRs function to form the antibody's folded structure, to support binding of CDRs, or the like.

The antibody may be an antibody that retains CDRs of the existing mouse anti-CD3 antibody, SP34, in which the amino acids of the constant domain (Fc) and the variable domain's FRs of SP34 are partially or entirely substituted with their human counterparts.

The antibody may comprise a light chain CDR1 including the amino acid sequence of SEQ ID NO: 29; a light chain CDR2 including the amino acid sequence of SEQ ID NO: 30; a light chain CDR3 including the amino acid sequence of SEQ ID NO: 31; a heavy chain CDR1 including the amino acid sequence of SEQ ID NO: 32; a heavy chain CDR2 including the amino acid sequence of SEQ ID NO: 33; and a heavy chain CDR3 including the amino acid sequence of SEQ ID NO: 34.

Accordingly, the antibody may be a humanized antibody that specifically binds to human CD3. As used herein, the term "humanized antibody" refers to a chimeric antibody that contains a minimal sequence derived from an immunoglobulin of a non-human antibody, such as a mouse antibody, and may mean such an antibody in which all parts except a sequence corresponding to a hypervariable region are substituted with their human counterparts.

In addition, the term "hypervariable region (HVR)" refers to a region of a variable domain which exhibits hypervariability or forms a structurally defined loop in the sequence of an antibody. Among definitions identifying the same, the complementarity determining region (CDR) definition according to Kabat is most commonly used to classify regions based on sequence variability.

For the antibody, an antibody fragment thereof may also be used as long as the antibody fragment maintains the antibody's function. The antibody or antibody fragment may include, but is not limited to, single-chain antibodies, diabodies, triabodies, tetrabodies, Fab fragments, F(ab')2 fragments, Fd's, scFv's, domain antibodies, minibodies, scAb's, IgD antibodies, IgE antibodies, IgM antibodies, IgG1 antibodies, IgG2 antibodies, IgG3 antibodies, IgG4 antibodies, derivatives of antibody's constant domains, artificial antibodies based on protein scaffolds, and the like, which maintain a binding function to CD3.

Meanwhile, the antibody may also be used in the form of an antibody-drug conjugate (ADC) obtained by binding of the antibody with an anticancer drug having tumor-cell proliferation inhibition efficacy. As used herein, the term "anticancer" includes "prevention" and "treatment" effects on cancer, and the "prevention" means any act of inhibiting or delaying cancer. In addition, the "treatment" means any act of ameliorating or beneficially altering symptoms of cancer.

The drug that can be used in the antibody-drug conjugate includes any compound having a cytotoxic or cytostatic effect, and a part or functional group of the compound. Examples of the drug include microtubulin structure formation inhibitors, meiosis inhibitors, RNA polymerase inhibitors, topoisomerase inhibitors, DNA intercalators, DNA alkylators, ribosomal inhibitors, miRNAs, shRNAs, siRNAs, radioisotopes, and toxins, among which at least one compound may be used.

The drug may include, but is not limited to, maytansinoid, auristatin, dolastatin, trichothecene, CC1065 (NSC 298223), calicheamicin, taxane, anthracycline, methotrexate, adriamycin, vindesine, vinca alkaloids (vincristine, vinblastine, etoposide), doxorubicin, melphalan, mitomycin C, chlorambucil, daunorubicin, daunomycin, etoposide, teniposide, carminomycin, aminopterin, dactinomycin, mitomycins, bleomycins, esperamicins, other enediyne antibiotics, 5-fluorouracil, other nitrogen mustards and stereoisomers, isosteres, homologs, or derivatives thereof, cis-platinum and cis-platinum homologs, other intercalator enzymes and fragments thereof, for example, nucleases, antibiotics, toxins (enzymatically active toxins or small molecule toxins of bacterial, fungal, plant, or animal origin), and various antitumor or anticancer agents such as cisplatin, CPT-11, paclitaxel, and docetaxel.

In addition, the radioisotope (radionuclide) includes 3H, 14C, 32P, 35S, 36Cl, 51Cr, 57Co, 58Co, 59Fe, 90Y, 125I, 131I, 186Re, and the like. MicroRNAs (miRNAs), siRNAs, shRNAs, and the like may also be used which can inhibit expression of certain oncogenes.

Binding of the anti-CD3 antibody with a drug is preferably achieved by conjugation using a functional group such as a thiol group of an amino acid residue such as lysine or cysteine in the antibody. If necessary, it is also possible to perform conjugation in a linker-mediated form which is commonly used. A maleimide- or iodine acetamide-based linker may also be used.

When a drug is conjugated to the antibody or a fragment thereof, the drug may be conjugated to the C-terminal site, which is opposite to an antigen binding site, from the viewpoint of decreasing an effect on the antibody or fragment's binding capacity and specificity to CD3, and the like. When the whole antibody, rather than a fragment thereof, is used, the drug may be conjugated to an Fc region.

In addition, the antibody may also be used as a chimeric antigen receptor (CAR)-based therapeutic agent containing the same. Examples of such a therapeutic agent preferably include, but are not limited to, chimeric antigen receptor T cell (CAR-T cell) or chimeric antigen receptor natural killer cell (CAR-NK cell) therapeutics.

The antibody may also be used in the form of a bispecific antibody containing an anti-CD3 antibody. The bispecific antibody is an antibody that has capacity of binding to two antigens at the same time, and may typically exist in a form in which heavy and light chain pairs that bind to different antigens are linked to each other.

In addition, the bispecific antibody is available in a form such as a bispecific single-chain antibody where single-chain antibody fragments (scFv's), in which VL and VH are linked to each other via a short linker peptide, are connected in the form of scFv1-scFv2(-Fc), a single-domain antibody (sdAb)-based dual antibody using VH, and a bispecific antibody generated using BiTE technology (see http://www.micromet.de) from Micromet, Germany.

The bispecific antibody may exist in a form in which the anti-CD3 antibody is bound to an antibody or a fragment thereof having binding capacity to an immunopotent cell-specific target molecule. The immunopotent cell-specific target molecule may preferably be selected from, but is not limited to, TCR/CD3, CD16 (FcγRIIIa), CD44, CD56, CD69, CD64 (FcγRI), CD89, and CD11b/CD18 (CR3).

In another aspect of the present invention, there is provided a polynucleotide that encodes the light chain variable domain (VL domain) and the heavy chain variable domain (VH domain) of the antibody according to the present invention and an expression vector comprising the same.

The polynucleotide that encodes the heavy chain variable domain of the antibody or an antibody fragment, that is, gene, may be easily derived by those skilled in the art from the amino acid sequence of the anti-CD3 antibody.

As used herein, the term "expression vector" refers to a recombinant vector capable of expressing a target protein in a host cell, and means a gene construct that contains essential regulatory elements operably linked thereto so that an inserted gene is expressed. The gene encoding the anti-CD3 antibody may be inserted into a separate vector or may be used in a form of being inserted into the same vector.

Specifically, the polynucleotide that encodes the amino acid sequence of the anti-CD3 antibody may be used in a form of being inserted into a separate or the same vector, and the polynucleotide that encodes the heavy chain or a variable domain thereof may be used in a form of being inserted into a separate or the same vector.

As used herein, the term "operably linked" means that a nucleic acid expression regulatory sequence and a nucleic acid sequence encoding a desired protein are functionally linked to perform a desired function. Operable linkage with a recombinant vector may be achieved using genetic recombination techniques well known in the art, and site specific DNA cleavage and ligation may be easily achieved using enzymes and the like commonly known in the art.

Expression vectors suitable for production of the anti-CD3 antibody may contain signal sequences for membrane targeting or secretion in addition to expression regulatory elements such as promoters, initiation codons, termination codons, polyadenylation signals, and enhancers. Initiation codons and termination codons are generally considered to be part of a nucleotide sequence encoding an immunogenic target protein. Such codons must be functional in a subject when a gene construct is administered and must be in frame with a coding sequence. In general, promoters may be constitutive or inducible. The promoter may include, but is not limited to, prokaryotic promoters such as lac, tac, T3, and T7, simian virus 40 (SV40) promoters, mouse breast tumor virus (MMTV) promoters, human immunodeficiency virus (HIV) promoters, for example, long terminal repeat (LTR) promoter of HIV, Moloney virus promoters, cytomegalovirus (CMV) promoters, Epstein bar virus (EBV) promoters, Rous sarcoma virus (RSV) promoters, as well as pi-actin promoters, human hemoglobin-, human muscle creatine-, human metallothionein-derived eukaryotic promoters, and the like.

The expression vector may further contain a selectable marker that allows for selection of host cells containing the same. The selectable marker is employed for selecting cells transformed with the vector. For the selectable marker, markers may be used which confer a selectable phenotype, such as drug resistance, auxotrophy, resistance to cytotoxic agents, or expression of surface proteins. In an environment treated with a selective agent, only cells expressing a selection marker survive, which allows for selection of transformed cells. In addition, when the vector is a replicable expression vector, such a vector may contain a replication origin that is a specific nucleic acid sequence from which replication is initiated.

As a recombinant expression vector for insertion of a foreign gene, various forms of vectors such as plasmids, viruses, and cosmids may be used. The type of recombinant vector is not particularly limited as long as the vector functions to express a desired gene and produce a desired protein in various host cells including prokaryotic and/or eukaryotic cells. The vector may preferably be a vector capable of producing a large amount of foreign protein that is in a form similar to its natural state while having a promoter with strong activity and strong expression capacity.

Various expression host/vector combinations may be used to express the anti-CD3 antibody. The expression vector suitable for eukaryotic hosts includes, but is not limited to, expression regulatory sequences derived from SV40, bovine papillomavirus, adenovirus, adeno-associated virus, cytomegalovirus, and retrovirus. The expression vector that may be used in bacterial hosts includes bacterial plasmids obtained from *Escherichia coli*, such as pET, pRSET, pBluescript, pGEX2T, pUC vector, colE1, pCR1, pBR322, pMB9, and derivatives thereof; plasmids having a wide host range such as RP4; phage DNAs that may be exemplified by a wide variety of phage lambda derivatives such as λgt10, λgt11, and NM989; and other DNA phages such as M13 and filamentous single-stranded DNA phages. The expression vector useful for yeast cells may include 2-micron plasmids and derivatives thereof. The vector useful for insect cells may be pVL941.

In yet another aspect of the present invention, there is provided a host cell, transformed with an expression vector according to the present invention. The expression vector may be inserted into a host cell to form a transformant. A suitable host cell for the vector may include prokaryotic cells such as *Escherichia coli, Bacillus subtilis, Streptomyces* sp., *Pseudomonas* sp., *Proteus mirabilis*, or *Staphylococcus* sp. In addition, the host cell may include eukaryotic cells including lower eukaryotic cells from fungi such as *Aspegillus* sp., yeasts such as *Pichia pastoris, Sacchammyces cerevisiae, Schizosacchammyces* sp., and *Neurospora crassa*, and other lower eukaryotes, and higher eukaryotic cells such as insect cells. In addition, the host cell may also be derived from plants or mammals. Preferably, the host cell that may be used includes, but is not limited to, monkey kidney cells (COS7 cells), NSO cells (myeloma cells of mouse origin), SP2/0 cells (myeloma cells of mouse origin), other myeloma cell lines, Chinese hamster ovary (CHO) cells, W138 cells (diploid human cell culture), baby hamster kidney (BHK) cells, MDCK, HuT 78 cells, HEK293 cells, and the like, with CHO cells being preferred.

As used herein, the term "transformation into host cells" is intended to include any method for introducing a nucleic acid into an organism, cell, tissue, or organ and, and such transformation may be performed using a standard technique as known in the art selected depending on the type of host cell. Specifically, electroporation, protoplast fusion, calcium phosphate ($CaPO_4$) precipitation, calcium chloride ($CaCl_2$) precipitation, agitation using silicon carbide fiber, agrobacterium-mediated transformation, PEG-, dextran sulfate-, lipofectamine-, or desiccation/inhibition-mediated transformation, or the like may be used. However, the present invention is not limited thereto.

In still yet another aspect of the present invention, there is provided a method for producing an antibody that specifically binds to CD3, comprising culturing the host cell. Specifically, the method for producing an antibody may comprise the steps of: inserting into a vector, a nucleotide sequence encoding the anti-CD3 antibody, to construct a recombinant vector; transforming a host cell with the recombinant vector and performing culture; and a step of separating and purifying a humanized antibody from the cultured transformant.

The humanized antibodies may be produced in a large amount by culturing the transformant, in which the recombinant vector is expressed, in a nutrient medium, and the medium and culture conditions may be appropriately selected from those known in the art depending on the type of host cell. During culture, conditions such as temperature, pH of a medium, and culture time may be appropriately adjusted to be suitable for cell growth and mass production of a protein.

The recombinantly produced anti-CD3 antibodies as described above may be recovered from a medium or a cell lysate. When the antibody is in a membrane-bound form, such an antibody may be liberated from the membrane using a suitable surfactant solution (for example, Triton-X 100) or by enzymatic cleavage. Cells used for expression of humanized antibodies may be disrupted by various physical and chemical means such as freeze-thaw cycles, sonication, mechanical disruption, or cell lysis agents, and separation and purification may be performed using conventional biochemical separation techniques. The biochemical separation technique that may be used includes, but is not limited to, electrophoresis, centrifugation, gel filtration, precipitation, dialysis, chromatography (ion-exchange chromatography, affinity chromatography, immunoabsorbent chromatography, size exclusion chromatography, or the like), isoelectric focusing, and the like.

In still yet another aspect of the present invention, there is provided a pharmaceutical composition for preventing or treating cancer, comprising an antibody according to the present invention or a fragment thereof.

The type of cancer that can be treated with the pharmaceutical composition may include both solid cancer and blood cancer, and preferably may include any cancers which express CD3. Here, the antibody may attract T cells through specific binding with CD3, and thus induce death of cancer cells.

Specifically, the cancer may be, but is not limited to, pancreatic cancer, liver cancer, gastric cancer, lung cancer, colorectal cancer, rectal cancer, thyroid cancer, esophageal cancer, kidney cancer, bladder cancer, prostate cancer, cervical cancer, breast cancer, blood cancer, skin cancer, epithelial cancer, brain cancer, central nerve system cancer, or ovarian cancer.

The pharmaceutical composition may further comprise a pharmaceutically acceptable carrier. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration.

Formulations of a pharmaceutical composition of the present invention may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms.

In addition, the pharmaceutical composition may contain a surfactant that can improve membrane permeability. These surfactants may be derived from steroids or may include cationic lipids such as N-[1-(2,3-dioleoyl)propyl-N,N,N-trimethylammonium chloride (DOTMA), or various compounds such as cholesterol hemisuccinate and phosphatidyl glycerol. However, the surfactant is not limited thereto.

In still yet another aspect of the present invention, there is provided a method for treating cancer or inhibiting cancer growth, comprising administering the pharmaceutical composition to a subject. The pharmaceutical composition comprising the anti-CD3 antibody may be administered in a pharmaceutically effective amount to treat cancer cells or metastases thereof or to inhibit cancer growth. The effective amount may vary depending on various factors such as type of cancer, the patient's age, weight, nature and severity of symptoms, type of current therapy, number of treatments, dosage form, and route of administration, and may be easily determined by experts in the corresponding field.

The pharmaceutical composition may be administered together or sequentially with the above-mentioned pharmacological or physiological components, and may also be administered in combination with additional conventional therapeutic agents, in which case the pharmaceutical composition may be administered sequentially or simultaneously with the conventional therapeutic agents. Such administration may be single or multiple administration. Taking all of the above factors into consideration, it is important to administer an amount that is a minimum amount and allows the maximum effect to be obtained without side effects, and such an amount may be easily determined by those skilled in the art.

As used herein, the term "subject" refers to a mammal, preferably human, suffering from or at risk of a condition or disease that can be alleviated, inhibited, or treated by administration of the pharmaceutical composition.

As used herein, the term "administration" means introducing a predetermined substance into a subject in any suitable manner, and the pharmaceutical composition may be administered via any route as long as the route allows the pharmaceutical composition to reach a target tissue. Such an administration method may include, but is not limited to, intraperitoneal administration, intravenous administration, intramuscular administration, subcutaneous administration, intradermal administration, oral administration, topical administration, intranasal administration, pulmonary administration, or rectal administration. Here, in case of being orally administered, from the viewpoint that proteins are digested, it may be desirable to formulate a composition for oral use so that an active agent is coated or the composition is protected from digestion in the stomach. In addition, the pharmaceutical composition may be administered by any device such that an active ingredient can migrate to its target cell.

In still yet another aspect of the present invention, there is provided a use of the antibody of the present invention for preventing or treating cancer.

In still yet another aspect of the present invention, there is provided a use of the antibody of the present invention for manufacture of a medicament for preventing or treating cancer.

In still yet another aspect of the present invention, there is provided a method for preventing or treating cancer, comprising administering the antibody of the present invention to a subject.

BEST MODE FOR CARRYING OUT THE INVENTION

Hereinafter, the present invention will be described in more detail by way of examples. The following examples are described for the purpose of illustrating the present invention, and the scope of the present invention is not limited thereto.

Example 1. Production of Humanized Anti-CD3 Antibody Candidates

Example 1.1. Selection of Candidate Antibodies for Humanization

The amino acid sequences of the light chain variable domain (VL domain) and heavy chain variable domain (VH domain) of mouse SP34, known as an anti-CD3 antibody, were entered into a web-based database (IgBLAST), and then the most similar human embryonic antibody sequences were searched. As a result, the highest amino acid sequence similarity was shown between the light chain variable region of mouse SP34 and *Homo sapiens* IGLV7-46*01 (IMGT gene name), and between the heavy chain variable domain of mouse SP34 and *Homo sapiens* IGHV3-73*02 (IMGT gene name).

Example 1.2. Humanization of Light Chain Variable Domain

The CDR amino acid sequence of *Homo sapiens* IGLV7-46*01 (IMGT gene name), a human embryonic antibody having a sequence most similar to the light chain variable domain of SP34, was replaced with the CDR sequence of mouse SP34, to prepare a partially humanized light chain variable domain of SP34.

In order to enhance antigen-binding properties of the partially humanized light chain variable domain of SP34, amino acid residues in the framework region (FR) sequences that are thought to play an important function in antigen-binding properties were replaced with the same amino acid residues as mouse SP34. The amino acid sequence of the humanized light chain variable domain of SP34 thus prepared is shown in Table 1 below.

Referring to Table 1, random modifications were made to the amino acid residues 38, 48, 51, and 71 of the light chain variable domain of mouse SP34, to prepare a total of 16 humanized light chain variable domains of SP34. Here, the light chain variable domain of mouse SP34 was used as a control for comparison of affinity to a CD3 antigen.

TABLE 1

| Clone | Variable domain | Amino acid sequence (Parts in bold indicate light chain CDR1, CDR2, CDR3 in order) | SEQ ID NO |
|---|---|---|---|
| 01 | Light chain | QAVVTQEPSLTVSPGGTVTLTCRSSTGAVT TSNYANWFQQKPGQAPRTLIYGTNKRAPWT PARFSGSLLGGKAALTLSGAQPEDEAEYYC ALWYSNLWVFGGGTKLTVLG | 1 |
| 02 | Light chain | QAVVTQEPSLTVSPGGTVTLTCRSSTGAVT TSNYANWFQQKPGQAPRTLIYGTNKRAPWT PARFSGSLLGDKAALTLSGAQPEDEAEYYC ALWYSNLWVFGGGTKLTVLG | 2 |
| 03 | Light chain | QAVVTQEPSLTVSPGGTVTLTCRSSTGAVT TSNYANWFQQKPGQAPRTLIGGTNKRAPWT PARFSGSLLGGKAALTLSGAQPEDEAEYYC ALWYSNLWVFGGGTKLTVLG | 3 |
| 04 | Light chain | QAVVTQEPSLTVSPGGTVTLTCRSSTGAVT TSNYANWFQQKPGQAPRTLIGGTNKRAPWT PARFSGSLLGDKAALTLSGAQPEDEAEYYC ALWYSNLWVFGGGTKLTVLG | 4 |
| 05 | Light chain | QAVVTQEPSLTVSPGGTVTLTCRSSTGAVT TSNYANWFQQKPGQAPRGLIYGTNKRAPWT PARFSGSLLGGKAALTLSGAQPEDEAEYYC ALWYSNLWVFGGGTKLTVLG | 5 |
| 06 | Light chain | QAVVTQEPSLTVSPGGTVTLTCRSSTGAVT TSNYANWFQQKPGQAPRGLIYGTNKRAPWT PARFSGSLLGDKAALTLSGAQPEDEAEYYC ALWYSNLWVFGGGTKLTVLG | 6 |
| 07 | Light chain | QAVVTQEPSLTVSPGGTVTLTCRSSTGAVT TSNYANWFQQKPGQAPRGLIGGTNKRAPWT PARFSGSLLGGKAALTLSGAQPEDEAEYYC ALWYSNLWVFGGGTKLTVLG | 7 |
| 08 | Light chain | QAVVTQEPSLTVSPGGTVTLTCRSSTGAVT TSNYANWFQQKPGQAPRGLIGGTNKRAPWT PARFSGSLLGDKAALTLSGAQPEDEAEYYC ALWYSNLWVFGGGTKLTVLG | 8 |
| 09 | Light chain | QAVVTQEPSLTVSPGGTVTLTCRSSTGAVT TSNYANWVQQKPGQAPRTLIYGTNKRAPWT PARFSGSLLGGKAALTLSGAQPEDEAEYYC ALWYSNLWVFGGGTKLTVLG | 9 |

TABLE 1-continued

| Clone | Variable domain | Amino acid sequence (Parts in bold indicate light chain CDR1, CDR2, CDR3 in order) | SEQ ID NO |
|---|---|---|---|
| 10 | Light chain | QAVVTQEPSLTVSPGGTVTLTCRSSTGAVT TSNYANWVQQKPGQAPRTLIYGTNKRAPWT PARFSGSLLGDKAALTLSGAQPEDEAEYYC ALWYSNLWVFGGGTKLTVLG | 10 |
| 11 | Light chain | QAVVTQEPSLTVSPGGTVTLTCRSSTGAVT TSNYANWVQQKPGQAPRTLIGGTNKRAPWT PARFSGSLLGDKAALTLSGAQPEDEAEYYC ALWYSNLWVFGGGTKLTVLG | 11 |
| 12 | Light chain | QAVVTQEPSLTVSPGGTVTLTCRSSTGAVT TSNYANWVQQKPGQAPRTLIGGTNKRAPWT PARFSGSLLGDKAALTLSGAQPEDEAEYYC ALWYSNLWVFGGGTKLTVLG | 12 |
| 13 | Light chain | QAVVTQEPSLTVSPGGTVTLTCRSSTGAVT TSNYANWVQQKPGQAPRGLIYGTNKRAPWT PARFSGSLLGDKAALTLSGAQPEDEAEYYC ALWYSNLWVFGGGTKLTVLG | 13 |
| 14 | Light chain | QAVVTQEPSLTVSPGGTVTLTCRSSTGAVT TSNYANWVQQKPGQAPRGLIYGTNKRAPWT PARFSGSLLGDKAALTLSGAQPEDEAEYYC ALWYSNLWVFGGGTKLTVLG | 14 |
| 15 | Light chain | QAVVTQEPSLTVSPGGTVTLTCRSSTGAVT TSNYANWVQQKPGQAPRGLIGGTNKRAPWT PARFSGSLLGDKAALTLSGAQPEDEAEYYC ALWYSNLWVFGGGTKLTVLG | 15 |
| 16 | Light chain | QAVVTQEPSLTVSPGGTVTLTCRSSTGAVT TSNYANWVQQKPGQAPRGLIGGTNKRAPWT PARFSGSLLGDKAALTLSGAQPEDEAEYYC ALWYSNLWVFGGGTKLTVLG | 16 |
| SP34 | Light chain | QAVVTQESALTTSPGETVTLTCRSSTGAVT TSNYANWVQEKPDHLFTGLIGGTNKRAPGV PARFSGSLIGDKAALTITGAQTEDEAIYFC ALWYSNLWVFGGGTKLTVLG | 17 |

Example 1.3. Humanization of Heavy Chain Variable Domain

The CDR amino acid sequence of *Homo sapiens* IGLV3-73*02 (IMGT gene name), a human embryonic antibody having a sequence most similar to the heavy chain variable domain of SP34, was replaced with the CDR sequence of mouse SP34, to prepare a partially humanized heavy chain variable domain of SP34.

In order to enhance antigen-binding properties of the partially humanized heavy chain variable domain of SP34, amino acid residues in the framework region (FR) sequences that are thought to play an important function in antigen-binding properties were replaced with the same amino acid residues as mouse SP34. The amino acid sequence of the humanized heavy chain variable domain of SP34 thus prepared is shown in Table 2 below.

Referring to Table 2, random modifications were made to amino acid residues 49, 78, 79, and 81 of the heavy chain variable domain of mouse SP34, to prepare a total of 8 humanized heavy chain variable domains of SP34. Here, the heavy chain variable domain of mouse SP34 was used as a control for comparison of affinity to a CD3 antigen.

TABLE 2

| Clone | Variable domain | Amino acid sequence (Parts in bold indicate heavy chain CDR1, CDR2, CDR3 in order) | SEQ ID NO |
|---|---|---|---|
| A | Heavy chain | EVQLVESGGGLVQPGGSLKLSCAASGFTFN TYAMNWVRQASGKGLEWVGRIRSKYNNYAT YYADSVKDRFTISRDDSKNTAYLQMNSLKT EDTAVYYCVRHGNFGNSYVSWFAYWGQGTL VTVSS | 18 |
| B | Heavy chain | EVQLVESGGGLVQPGGSLKLSCAASGFTFN TYAMNWVRQASGKGLEWVGRIRSKYNNYAT YYADSVKDRFTISRDDSKNTLYLQMNSLKT EDTAVYYCVRHGNFGNSYVSWFAYWGQGTL VTVSS | 19 |
| C | Heavy chain | EVQLVESGGGLVQPGGSLKLSCAASGFTFN TYAMNWVRQASGKGLEWVGRIRSKYNNYAT YYADSVKDRFTISRDDSQSTAYLQMNSLKT EDTAVYYCVRHGNFGNSYVSWFAYWGQGTL VTVSS | 20 |
| D | Heavy chain | EVQLVESGGGLVQPGGSLKLSCAASGFTFN TYAMNWVRQASGKGLEWVGRIRSKYNNYAT YYADSVKDRFTISRDDSQSTLYLQMNSLKT EDTAVYYCVRHGNFGNSYVSWFAYWGQGTL VTVSS | 21 |
| E | Heavy chain | EVQLVESGGGLVQPGGSLKLSCAASGFTFN TYAMNWVRQASGKGLEWVARIRSKYNNYAT YYADSVKDRFTISRDDSKNTAYLQMNSLKT EDTAVYYCVRHGNFGNSYVSWFAYWGQGTL VTVSS | 22 |
| F | Heavy chain | EVQLVESGGGLVQPGGSLKLSCAASGFTFN TYAMNWVRQASGKGLEWVARIRSKYNNYAT YYADSVKDRFTISRDDSKNTLYLQMNSLKT EDTAVYYCVRHGNFGNSYVSWFAYWGQGTL VTVSS | 23 |
| G | Heavy chain | EVQLVESGGGLVQPGGSLKLSCAASGFTFN TYAMNWVRQASGKGLEWVARIRSKYNNYAT YYADSVKDRFTISRDDSQSTAYLQMNSLKT EDTAVYYCVRHGNFGNSYVSWFAYWGQGTL VTVSS | 24 |
| H | Heavy chain | EVQLVESGGGLVQPGGSLKLSCAASGFTFN TYAMNWVRQASGKGLEWVARIRSKYNNYAT YYADSVKDRFTISRDDSQSTLYLQMNSLKT EDTAVYYCVRHGNFGNSYVSWFAYWGQGTL VTVSS | 25 |
| SP34 | Heavy chain | EVQLVESGGGLVQPKGSLKLSCAASGFTFN TYAMNWVRQAPGKGLEWVARIRSKYNNYAT YYADSVKDRFTISRDDSQSILYLQMNNLKT EDTAMYYCVRHGNFGNSYVSWFAYWGQGTL VTVSS | 26 |

Example 1.4. Cloning of Humanized Anti-CD3 Antibody Candidates

Each of the genes for the 16 light chain variable domains as prepared above was inserted into pcDNA3.4 animal cell expression vector containing a lambda light chain constant domain (λ-CL), and each of the genes for the 8 heavy chain variable domains was inserted into pcDNA3.4 animal cell expression vector containing IgG1 constant domains (CH1, hinge, CH2, CH3).

The respective specific amino acid sequences for the lambda light chain constant domain and the IgG1 heavy chain constant domain are shown in Table 3 below.

TABLE 3

| Clone | Constant domain | Amino acid sequence | SEQ ID NO |
|---|---|---|---|
| λ | Light chain | QPKANPTVTLFPPSSEELQANKATLVCLIS DFYPGAVTVAWKADGSPVKAGVETTKPSKQ SNNKYAASSYLSLTPEQWKSHRSYSCQVTH EGSTVEKTVAPTEC | 27 |
| IgG1 | Heavy chain | ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPEAAGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSRDE LTKNQVSLTCLVKGFYPSDIAVEWESNGQP ENNYKTTPPVLDSDGSFFLYSKLTVDKSRW QQGNVFSCSVMHEALHNHYTQKSLSLSPGK | 28 |

Example 1.5. Transfection of Humanized Anti-CD3 Antibody Candidates

Twenty-four hours before transfection, Expi293F cells at a density of $2.0 \times 10^6$ cells/ml were passaged with Expi293 medium at $125 \pm 10$ rpm in a shaking incubator at a condition of 37° C. and 8% $CO_2$. When transfection was performed, the number of cells and cell viability were measured to identify whether cell viability of 95% or higher was exhibited.

The cells were dispensed at $7.5 \times 10^7$ cells in a 125 mL culture flask, and then Expi293 medium was added to adjust the final volume to 25 mL (based on 30 ML). Using Opti-MEM I medium, 30 μg of antibody-expressing vector was mixed therewith to a total of 1.5 ml and incubation was performed for 5 minutes at room temperature. For the antibody vectors, a total of 128 humanized SP34 IgG1 antibodies, obtained by combination of the expression vectors for 8 heavy chain variable domains and the expression vectors for 16 light chain variable domains, were used. Mouse human chimeric SP34 IgG1 antibody was used as a control antibody vector. The specific antibody combinations are shown in Table 4 below.

TABLE 4

| | | Heavy chain (VH) | | | | | | | |
|---|---|---|---|---|---|---|---|---|---|
| Clone | | A | B | C | D | E | F | G | H |
| Light chain (VL) | 01 | A01 | B01 | C01 | D01 | E01 | F01 | G01 | H01 |
| | 02 | A02 | B02 | C02 | D02 | E02 | F02 | G02 | H02 |
| | 03 | A03 | B03 | C03 | D03 | E03 | F03 | G03 | H03 |
| | 04 | A04 | B04 | C04 | D04 | E04 | F04 | G04 | H04 |
| | 05 | A05 | B05 | C05 | D05 | E05 | F05 | G05 | H05 |
| | 06 | A06 | B06 | C06 | D06 | E06 | F06 | G06 | H06 |
| | 07 | A07 | B07 | C07 | D07 | E07 | F07 | G07 | H07 |
| | 08 | A08 | B08 | C08 | D08 | E08 | F08 | G08 | H08 |
| | 09 | A09 | B09 | C09 | D09 | E09 | F09 | G09 | H09 |
| | 10 | A10 | B10 | C10 | D10 | E10 | F10 | G10 | H10 |
| | 11 | A11 | B11 | C11 | D11 | E11 | F11 | G11 | H11 |
| | 12 | A12 | B12 | C12 | D12 | E12 | F12 | G12 | H12 |
| | 13 | A13 | B13 | C13 | D13 | E13 | F13 | G13 | H13 |
| | 14 | A14 | B14 | C14 | D14 | E14 | F14 | G14 | H14 |
| | 15 | A15 | B15 | C15 | D15 | E15 | F15 | G15 | H15 |
| | 16 | A16 | B16 | C16 | D16 | E16 | F16 | G16 | H16 |

Using Opti-MEM I medium, 80 μl of transfection reagent was mixed therewith to a total of 1.5 ml, and incubation was performed at room temperature for 5 minutes. The Opti-MEM I media respectively containing the vector and the transfection reagent were gently mixed and allowed to react at room temperature for 20 minutes. Then, the resultant was placed in the flask containing Expi293F cells. Incubation was performed at $125 \pm 10$ rpm for 16 to 20 hours in a shaking incubator at a condition of 37° C. and 8% $CO_2$. Then, 1.5 ml of transfection enhancer I and 150 μl of transfection enhancer II were added thereto, and incubation was performed for 6 days to obtain candidate antibodies.

Example 1.6. Purification of Antibodies

The incubation was centrifuged at 4,000 rpm for 30 minutes, filtered through a 0.22 μm filter, and then cell debris was removed to obtain the supernatant. 0.2 ml of Mabselect Xtra resin was added to a column, and equilibration was performed using Protein A binding buffer in a volume corresponding to 10 times the resin volume.

Subsequently, the supernatant was loaded onto the column using gravity. After the loading was completed, the column was washed with Protein A binding buffer in a volume corresponding to 10 times the resin volume.

Subsequently, IgG elution buffer was added to the column and elution was performed. The eluate was neutralized by adding 25 μl of 1.5 M Tris-Cl per 1 ml of the eluate. Then, the eluate concentration was measured at an OD of 280 nm. The eluant for which the concentration had been measured was subjected to buffer exchange with PBS via dialysis.

Example 2. Selection of Humanized Anti-CD3 Antibodies

Enzyme-linked immunosorbent assay (ELSA) was used to select antibodies showing affinity to human CD3 and monkey CD3 among a total of 128 anti-CD3 antibody (SP34) combinations.

Specifically, recombinant human or cynomolgus monkey CD3ε/δ heterodimer was diluted in a coating buffer and used to treat a 96-well-plate. The plate was stored at 4° C. for 12 hours or longer. Subsequently, the buffer was removed and treatment with a 1% bovine serum albumin (BSA)/PBS solution was performed at room temperature for 1 hour. Then, the solution was removed. The recombinant CD3-coated wells were then treated with antibody-expressing culture solutions for about 1 hour.

The wells were washed with a 0.05% Tween 20/PBS solution, and then treatment with the human IgG antibody conjugated with horseradish peroxidase, which had been diluted in a 1% BSA-PBS solution, was performed at room temperature for 1 hour. Then, the solution was removed and the wells were washed with a 0.05% Tween 20/PBS solution.

A TMB (3,3',5,5'-tetramethylbenzidine) solution was used to treat the 96-well-plate, and the 96-well-plate was left to stand at room temperature for 30 minutes. Then, treatment with a stop solution was performed, and the degree of color development was immediately determined at an absorbance wavelength of 450 nm. Among the humanized SP34 antibody candidates, only those samples that developed color were clones that maintained affinity to CD3 of the mouse SP34 antibody. The specific results obtained by affinity measurement are shown in Table 5 below.

TABLE 5

| Clone | Absorbance (450 nm) BSA | human CD3 | cyno CD3 |
|---|---|---|---|
| A01 | 0.107 | 0.152 | 0.098 |
| A02 | 0.071 | 0.098 | 0.068 |
| A03 | 0.092 | 0.132 | 0.094 |
| A04 | 0.063 | 0.098 | 0.065 |
| A05 | 0.152 | 0.167 | 0.141 |
| A06 | 0.084 | 0.140 | 0.108 |
| A07 | 0.089 | 1.315 | 2.546 |
| A08 | 0.094 | 0.875 | 2.339 |
| A09 | 0.061 | 0.092 | 0.050 |
| A10 | 0.077 | 0.097 | 0.066 |
| A11 | 0.072 | 0.122 | 0.105 |
| A12 | 0.060 | 0.097 | 0.068 |
| A13 | 0.098 | 0.172 | 0.154 |
| A14 | 0.082 | 0.125 | 0.113 |
| A15 | 0.099 | 2.785 | 2.864 |
| A16 | 0.068 | 2.538 | 2.799 |
| B01 | 0.055 | 0.097 | 0.071 |
| B02 | 0.059 | 0.086 | 0.072 |
| B03 | 0.071 | 0.126 | 0.091 |
| B04 | 0.053 | 0.087 | 0.059 |
| B05 | 0.069 | 0.102 | 0.100 |
| B06 | 0.077 | 0.138 | 0.143 |
| B07 | 0.061 | 0.718 | 2.449 |
| B08 | 0.060 | 0.424 | 2.193 |
| B09 | 0.063 | 0.096 | 0.099 |
| B10 | 0.078 | 0.098 | 0.076 |
| B11 | 0.074 | 0.132 | 0.107 |
| B12 | 0.059 | 0.098 | 0.072 |
| B13 | 0.130 | 0.169 | 0.156 |
| B14 | 0.078 | 0.127 | 0.102 |
| B15 | 0.204 | 2.709 | 3.161 |
| B16 | 0.064 | 2.370 | 2.926 |
| C01 | 0.128 | 0.131 | 0.075 |
| C02 | 0.108 | 0.099 | 0.071 |
| C03 | 0.126 | 0.140 | 0.089 |
| C04 | 0.073 | 0.093 | 0.067 |
| C05 | 0.099 | 0.107 | 0.128 |
| C06 | 0.080 | 0.108 | 0.083 |
| C07 | 0.113 | 0.960 | 2.604 |
| C08 | 0.111 | 0.446 | 2.178 |
| C09 | 0.083 | 0.109 | 0.075 |
| C10 | 0.066 | 0.096 | 0.074 |
| C11 | 0.168 | 0.288 | 0.261 |
| C12 | 0.065 | 0.087 | 0.065 |
| C13 | 0.128 | 0.179 | 0.179 |
| C14 | 0.075 | 0.107 | 0.095 |
| C15 | 0.098 | 2.454 | 2.813 |
| C16 | 0.092 | 2.369 | 2.802 |
| D01 | 0.124 | 0.136 | 0.099 |
| D02 | 0.056 | 0.150 | 0.073 |
| D03 | 0.073 | 0.159 | 0.130 |
| D04 | 0.083 | 0.091 | 0.072 |
| D05 | 0.061 | 0.121 | 0.101 |
| D06 | 0.092 | 0.136 | 0.110 |
| D07 | 0.074 | 1.168 | 2.393 |
| D08 | 0.083 | 0.897 | 2.532 |
| D09 | 0.083 | 0.122 | 0.098 |
| D10 | 0.076 | 0.117 | 0.113 |
| D11 | 0.105 | 0.138 | 0.134 |
| D12 | 0.081 | 0.095 | 0.114 |
| D13 | 0.314 | 0.569 | 0.532 |
| D14 | 0.121 | 0.149 | 0.113 |
| D15 | 0.108 | 2.529 | 3.006 |
| D16 | 0.080 | 2.655 | 2.872 |
| E01 | 0.078 | 0.100 | 0.078 |
| E02 | 0.077 | 0.095 | 0.070 |
| E03 | 0.098 | 0.134 | 0.076 |
| E04 | 0.080 | 0.087 | 0.067 |
| E05 | 0.083 | 0.085 | 0.068 |
| E06 | 0.206 | 0.112 | 0.086 |
| E07 | 0.097 | 0.109 | 0.115 |
| E08 | 0.106 | 0.074 | 0.099 |
| E09 | 0.072 | 0.096 | 0.084 |
| E10 | 0.064 | 0.083 | 0.065 |
| E11 | 0.065 | 0.098 | 0.075 |
| E12 | 0.059 | 0.088 | 0.064 |

TABLE 5-continued

| Clone | Absorbance (450 nm) BSA | human CD3 | cyno CD3 |
|---|---|---|---|
| E13 | 0.085 | 0.139 | 0.114 |
| E14 | 0.068 | 0.105 | 0.078 |
| E15 | 0.130 | 2.411 | 2.702 |
| E16 | 0.089 | 2.399 | 2.736 |
| F01 | 0.084 | 0.118 | 0.086 |
| F02 | 0.062 | 0.093 | 0.076 |
| F03 | 0.078 | 0.128 | 0.101 |
| F04 | 0.057 | 0.084 | 0.069 |
| F05 | 0.066 | 0.105 | 0.075 |
| F06 | 0.079 | 0.115 | 0.096 |
| F07 | 0.142 | 0.133 | 0.163 |
| F08 | 0.076 | 0.134 | 0.180 |
| F09 | 0.071 | 0.099 | 0.084 |
| F10 | 0.068 | 0.118 | 0.091 |
| F11 | 0.071 | 0.138 | 0.104 |
| F12 | 0.090 | 0.090 | 0.077 |
| F13 | 0.076 | 0.192 | 0.151 |
| F14 | 0.071 | 0.114 | 0.100 |
| F15 | 0.081 | 2.489 | 2.755 |
| F16 | 0.066 | 2.455 | 2.855 |
| G01 | 0.080 | 0.113 | 0.096 |
| G02 | 0.075 | 0.146 | 0.069 |
| G03 | 0.078 | 0.098 | 0.088 |
| G04 | 0.067 | 0.129 | 0.063 |
| G05 | 0.079 | 0.109 | 0.072 |
| G06 | 0.095 | 0.118 | 0.078 |
| G07 | 0.077 | 0.118 | 0.316 |
| G08 | 0.148 | 0.137 | 0.119 |
| G09 | 0.083 | 0.106 | 0.079 |
| G10 | 0.072 | 0.099 | 0.079 |
| G11 | 0.086 | 0.104 | 0.080 |
| G12 | 0.057 | 0.085 | 0.065 |
| G13 | 0.132 | 0.265 | 0.242 |
| G14 | 0.075 | 0.105 | 0.099 |
| G15 | 0.091 | 2.415 | 2.694 |
| G16 | 0.108 | 2.482 | 2.773 |
| H01 | 0.087 | 0.121 | 0.154 |
| H02 | 0.125 | 0.111 | 0.080 |
| H03 | 0.068 | 0.113 | 0.085 |
| H04 | 0.055 | 0.077 | 0.068 |
| H05 | 0.059 | 0.078 | 0.061 |
| H06 | 0.086 | 0.134 | 0.101 |
| H07 | 0.060 | 0.110 | 0.090 |
| H08 | 0.091 | 0.118 | 0.136 |
| H09 | 0.085 | 0.141 | 0.113 |
| H10 | 0.055 | 0.088 | 0.077 |
| H11 | 0.083 | 0.122 | 0.142 |
| H12 | 0.060 | 0.099 | 0.083 |
| H13 | 0.083 | 0.175 | 0.196 |
| H14 | 0.064 | 0.096 | 0.094 |
| H15 | 0.067 | 2.436 | 2.836 |
| H16 | 0.080 | 2.461 | 2.873 |

As can be seen from the results in Table 5 above, it was shown that 24 clones, A7, A8, A15, A16, B7, B8, B15, B16, C7, C8, C15, C16, D7, D8, D15, D16, E15, E16, F15, F16, G15, G16, H15, and H16, maintained affinity to human CD3 and monkey CD3. Thus, these 24 clones were selected as humanized anti-CD3 antibodies (SP34).

Example 3. Measurement of Affinity to Recombinant CD3 of Humanized Anti-CD3 Antibodies The Octet system was used to measure affinity to recombinant CD3 of the humanized anti-CD3 antibodies (SP34) selected in accordance with Example 2.

Specifically, recombinant human or monkey CD3ε/δ was prepared at a concentration of 5 μg/ml in 1× kinetic buffer and used to treat a 96-well-plate at 200 μl/well. The CD3ε/δ after treatment was fixed to the anti-Penta His (HIS1K, Cat #18-5121, Fortebio) sensor.

The clones showing binding affinity to the recombinant human or monkey CD3ε/δ in the ELISA results were prepared at a concentration of 50 nM in 1× kinetic buffer, and treatment therewith was performed at 200 µl/well. The 1× kinetic buffer was obtained by diluting 10× kinetic buffer (ForteBio, Cat #18-1092) 10 times with PBS and used.

The interaction between the CD3ε/δ fixed to the sensor and the antibody at a concentration of 50 nM was analyzed to calculate antigen-antibody affinity, and the results are shown in Table 6 below.

TABLE 6

| Ag | Human CD3E/D | | | Cyno CD3E/D | | |
|---|---|---|---|---|---|---|
| Clone | KD (M) | kon(1/Ms) | kdis(1/s) | KD (M) | kon(1/Ms) | kdis(1/s) |
| cSP34 | 2.29E−10 | 2.62E+05 | 6.01E−05 | 1.40E−10 | 3.78E+05 | 5.30E−05 |
| A7 | 1.95E−08 | 1.19E+05 | 2.32E−03 | 2.05E−08 | 1.53E+05 | 3.15E−03 |
| B7 | 2.14E−08 | 1.98E+05 | 4.23E−03 | 3.09E−08 | 2.08E+05 | 6.42E−03 |
| C7 | 2.30E−08 | 1.52E+05 | 3.49E−03 | 2.75E−08 | 1.94E+05 | 5.35E−03 |
| D7 | 1.90E−08 | 1.13E+05 | 2.14E−03 | 2.00E−08 | 1.43E+05 | 2.84E−03 |
| A8 | 2.22E−08 | 1.02E+05 | 2.26E−03 | 2.19E−08 | 1.47E+05 | 3.21E−03 |
| B8 | 2.76E−08 | 1.48E+05 | 4.07E−03 | 2.63E−08 | 1.99E+05 | 5.25E−03 |
| C8 | 2.94E−08 | 1.08E+05 | 3.17E−03 | 3.56E−08 | 1.66E+05 | 5.89E−03 |
| D8 | 3.50E−08 | 8.20E+04 | 2.87E−03 | 2.16E−08 | 1.23E+05 | 2.66E−03 |
| A15 | 2.96E−10 | 3.23E+05 | 9.58E−05 | 3.64E−10 | 4.53E+05 | 1.65E−04 |
| B15 | 5.21E−10 | 3.71E+05 | 1.93E−04 | 6.27E−10 | 5.23E+05 | 3.28E−04 |
| C15 | 4.30E−10 | 3.76E+05 | 1.62E−04 | 6.53E−10 | 5.25E+05 | 3.43E−04 |
| D15 | 2.94E−10 | 3.27E+05 | 9.60E−05 | 5.33E−10 | 4.37E+05 | 2.33E−04 |
| E15 | 1.74E−09 | 2.25E+05 | 3.92E−04 | 1.86E−09 | 2.90E+05 | 5.40E−04 |
| F15 | 1.04E−09 | 1.97E+05 | 2.06E−04 | 1.33E−09 | 2.24E+05 | 2.97E−04 |
| G15 | 1.59E−09 | 2.09E+05 | 3.32E−04 | 1.72E−09 | 2.69E+05 | 4.61E−04 |
| H15 | 9.53E−10 | 1.99E+05 | 1.89E−04 | 1.17E−09 | 2.30E+05 | 2.69E−04 |
| A16 | 2.93E−10 | 2.75E+05 | 8.07E−05 | 6.57E−10 | 3.70E+05 | 2.43E−04 |
| B16 | 4.45E−10 | 3.22E+05 | 1.44E−04 | 6.60E−10 | 4.66E+05 | 3.08E−04 |
| C16 | 4.19E−10 | 2.68E+05 | 1.12E−04 | 8.88E−10 | 3.84E+05 | 3.41E−04 |
| D16 | 4.46E−10 | 2.40E+05 | 1.07E−04 | 6.11E−10 | 3.56E+05 | 2.17E−04 |
| E16 | 1.76E−09 | 1.62E+05 | 2.84E−04 | 2.19E−09 | 2.20E+05 | 4.82E−04 |
| F16 | 8.52E−10 | 1.41E+05 | 1.20E−04 | 1.37E−09 | 1.85E+05 | 2.53E−04 |
| G16 | 1.32E−09 | 1.53E+05 | 2.01E−04 | 1.75E−09 | 1.95E+05 | 3.40E−04 |
| H16 | 8.81E−10 | 1.36E+05 | 1.20E−04 | 1.13E−09 | 1.82E+05 | 2.06E−04 |

As can be seen from the results in Table 6, it was identified that all the clones show excellent affinity to both human and monkey CD3ε/δ; and among these, Clones A15, B15, C15, D15, A16, B16, C16, and D16 show the best affinity.

Example 4. Measurement of Affinity to Human T Cells of Humanized Anti-CD3 Antibodies Flow cytometry was used to measure affinity to human T cells of the humanized anti-CD3 antibodies (SP34) selected in accordance with Example 2.

Specifically, H9 (ATCC® HTB-176TM) cells were prepared at 2×10$^5$ cells in 100 µl FACS buffer (1% FBS/FACS sheath) per antibody sample, and then 1 µg of antibody was used to treat the cells. The resultant was stored for 25 minutes in the dark at 4° C. Subsequently, treatment with 3 ml of FACS buffer was performed, and centrifugation was performed at 2,000 rpm for 3 minutes. Then, the supernatant was discarded.

Next, 100 µl FACS buffer containing 1 µg of phycoerythrin (PE)-conjugated human IgG antibody was used to treat the cells, and the resultant was stored for 25 minutes in the dark at 4° C. Subsequently, treatment with 3 ml of FACS buffer was performed, and centrifugation was performed at 2,000 rpm for 3 minutes. Then, the supernatant was discarded.

The cells were treated with a 4% formaldehyde solution, stored in the dark at 4° C. for 30 minutes, and then treated with 3 ml of FACS buffer. Centrifugation was performed at 2,000 rpm for 3 minutes, and then the supernatant was discarded. Treatment with 350 µl of FACS buffer was performed, and a flow cytometer was used to perform affinity analysis of the antibodies for the human T cells. The analysis results are illustrated in FIG. 1.

Referring to FIG. 1, it was found that all antibodies, which had bound to recombinant human CD3ε/δ, also specifically bound to human T cells.

Example 5. Measurement of Affinity to Monkey T Cells of Humanized Anti-CD3 Antibodies Flow cytometry was used to measure affinity to monkey T cells of the humanized anti-CD3 antibodies (SP34) selected in accordance with Example 2.

Specifically, monkey splenocytes were prepared at 10$^6$ cells in 100 µl FACS solution per antibody sample, and then 1 µg of antibody was used to treat the cells. The resultant was stored for 25 minutes in the dark at 4° C. Subsequently, treatment with 3 ml of FACS buffer was performed, and centrifugation was performed at 2,000 rpm for 3 minutes. Then, the supernatant was discarded.

Next, 100 µl FACS buffer containing 1 µg of PE-conjugated human IgG antibody was used to treat the cells, and the resultant was stored for 25 minutes in the dark at 4° C. Subsequently, treatment with 3 ml of FACS buffer was performed, and centrifugation was performed at 2,000 rpm for 3 minutes. Then, the supernatant was discarded.

The cells were treated with FITC-conjugated anti-CD20 antibody, PE-Cy5-conjugated anti-CD14, 7-AAD antibody, APC-Cy7-conjugated anti-CD16 antibody, or V450-conjugated anti-CD45 antibody, and the resultant was stored for 25 minutes in the dark at 4° C. Subsequently, treatment with 3 ml of FACS buffer was performed, and centrifugation was performed at 2,000 rpm for 3 minutes. Then, the supernatant was discarded.

The cells were treated with a 4% formaldehyde solution, stored in the dark at 4° C. for 30 minutes, and then treated with 3 ml of FACS buffer. Centrifugation was performed at 2,000 rpm for 3 minutes, and then the supernatant was discarded. Treatment with 350 µl of FACS buffer was performed, and a flow cytometer was used to perform affinity analysis of the antibodies for the human T cells. The analysis results are illustrated in FIG. 2.

Referring to FIG. 2, it was found that all antibodies, which had bound to recombinant monkey CD3ε/δ, also specifically bound to monkey T cells.

Although the embodiments have been described by a limited number of examples and the drawings as described above, it will be apparent to those skilled in the art that various changes and modifications may be made without departing from the spirit and scope of the invention. For example, it is possible to achieve desired results even in a case where the techniques as described are performed in a different order than the described method, and/or the components as described are assembled or combined in a different form than the described method, or replaced or substituted by other components or equivalents.

Therefore, other implementations, other embodiments, and equivalents of the appended claims fall within the scope of the appended claims.

The invention claimed is:

1. An antibody or an antigen-binding fragment thereof, said antigen or antigen-binding fragment thereof comprising:
   - (a-1) a light chain variable domain (VL domain) comprising the amino acid sequence of SEQ ID NO: 7 or 8; and
   - (a-2) a heavy chain variable domain (VH domain) comprising the amino acid sequence of SEQ ID NO: 18, 19, 20, or 21, or (b-1) a light chain variable domain (VL domain) comprising the amino acid sequence of SEQ ID NO: 15 or 16; and
   - (b-2) a heavy chain variable domain (VH domain) comprising the amino acid sequence of SEQ ID NO: 18, 19, 20, 21, 22, 23, 24, or 25,
   - wherein the VL domain of (a-1) and (b-1) comprises complementarity determining region (CDR)1 comprising the amino acid sequence of SEQ ID NO: 29, CDR2 comprising the amino acid sequence of SEQ ID NO: 30, and CDR3 comprising the amino acid sequence of SEQ ID NO: 31; and
   - wherein the VH domain of (a-2) and (b-2) comprises complementarity determining region (CDR)1 comprising the amino acid sequence of SEQ ID NO: 32, CDR2 comprising the amino acid sequence of SEQ ID NO: 33, and CDR3 comprising the amino acid sequence of SEQ ID NO: 34.

2. The antibody or the antigen-binding fragment thereof of claim 1, wherein the antibody or the antigen-binding fragment thereof specifically binds to cluster of differentiation 3 (CD3).

3. The antibody or the antigen-binding fragment thereof of claim 2, wherein the CD3 includes human-derived CD3 and monkey-derived CD3.

4. The antibody or the antigen-binding fragment thereof of claim 1, wherein the antibody or the antigen-binding fragment thereof specifically binds to T cells.

5. The antibody or the antigen-binding fragment thereof of claim 4, wherein the T cells include human-derived T cells and monkey-derived T cells.

6. The antibody or the antigen-binding fragment thereof of claim 1, wherein the antibody is a humanized antibody.

7. A polynucleotide that encodes the light chain variable domain (VL domain) and the heavy chain variable domain (VH domain) of the antibody or the antigen-binding fragment thereof of claim 1.

8. An expression vector comprising the polynucleotide of claim 7.

9. A host cell transformed with the expression vector of claim 8.

10. A method for producing an antibody that specifically binds to CD3, comprising culturing the host cell of claim 9.

11. A pharmaceutical composition comprising the antibody or the antigen-biding fragment thereof of claim 1.

12. A pharmaceutical composition comprising the antibody or the antigen-biding fragment thereof of claim 2.

13. A pharmaceutical composition comprising the antibody or the antigen-biding fragment thereof of claim 3.

14. A pharmaceutical composition comprising the antibody or the antigen-biding fragment thereof of claim 4.

15. A pharmaceutical composition comprising the antibody or the antigen-biding fragment thereof of claim 5.

16. A pharmaceutical composition comprising the antibody or the antigen-biding fragment thereof of claim 6.

* * * * *